(12) United States Patent
Grisoni

(10) Patent No.: US 7,147,666 B1
(45) Date of Patent: Dec. 12, 2006

(54) MONOLITHIC IMPLANTS WITH OPENINGS

(76) Inventor: Bernard Francis Grisoni, 9160 Highway 64, Suite 12, Arlington, TN (US) 38002

(*) Notice: Subject to any disclaimer, the term of this patent is extended or adjusted under 35 U.S.C. 154(b) by 0 days.

(21) Appl. No.: 08/979,097

(22) Filed: Nov. 26, 1997

(51) Int. Cl.
*A61F 2/02* (2006.01)

(52) U.S. Cl. .................. 623/23.51; 623/16.11
(58) Field of Classification Search ........... 623/16.11, 623/23.51–23.61, 23.72–23, 11.11, 23.48, 623/23.5; 606/76–77; 433/201.1; 424/422, 424/426
See application file for complete search history.

(56) References Cited

U.S. PATENT DOCUMENTS

| | | | | |
|---|---|---|---|---|
| 4,195,366 A | * | 4/1980 | Jarcho et al. ............ 623/23.56 |
| 4,596,574 A | * | 6/1986 | Urist ........................ 424/422 |
| 4,619,655 A | | 10/1986 | Hanker et al. |
| 4,794,046 A | * | 12/1988 | Nagai ........................ 623/16 |
| 5,112,354 A | * | 5/1992 | Sires ........................ 623/16 |
| 5,141,510 A | * | 8/1992 | Takagi et al. ............... 623/16 |
| 5,147,403 A | | 9/1992 | Gitelis |
| 5,236,459 A | * | 8/1993 | Koch et al. ................ 623/16 |
| 5,290,494 A | * | 3/1994 | Coombes et al. ........... 264/41 |
| 5,425,769 A | * | 6/1995 | Snyders, Jr. ............ 623/23.61 |
| 5,490,962 A | * | 2/1996 | Cima et al. ............... 264/401 |
| 5,514,180 A | * | 5/1996 | Heggeness et al. ......... 623/71 |
| 5,518,680 A | * | 5/1996 | Cima et al. ............... 264/401 |
| 5,522,895 A | * | 6/1996 | Mikos .................... 623/23.58 |
| 5,531,794 A | * | 7/1996 | Takagi et al. ............... 623/16 |
| 5,569,308 A | | 10/1996 | Sottosanti |
| 5,614,206 A | | 3/1997 | Randolph et al. |
| 5,626,861 A | * | 5/1997 | Laurencin et al. .......... 424/426 |
| 5,639,402 A | * | 6/1997 | Barlow et al. ................ 264/6 |
| 5,683,461 A | * | 11/1997 | Lee et al. .................... 623/16 |
| 5,727,945 A | * | 3/1998 | Dannenbaum .............. 433/215 |
| 5,728,510 A | * | 3/1998 | White ........................ 430/323 |
| 6,013,853 A | * | 1/2000 | Athanasiou et al. ........ 424/423 |

OTHER PUBLICATIONS

Coetzee, A.S. et al., "Regeneration of Bone in the Presence of Calcium Sulfate", *Arch Otolaryngol*, 106:405–409 (1980).

Bouillet, R. et al., "Traitement de L'Osteomyelete Chronique en Milieu Africain Par Implant De Platre Impregne D';antibiotiques", *Acta Orthopaedica Belgica*, 55:1–11 (1989).

Mackey, D. et al., "Antibiotic Loaded Plaster of Paris Pellets", *Clin. Ortho. and Rel. Res.*, 167:263–268 (1982).

Peltier, L. et al., "Calcium Sulfate" in *Bone Graft and Bone Substitute*, Chapter 22:243–246 (1993).

Sulo, I, "The Use of Gentamycin Impregnated Plaster Beads in the Treatment of Bone Infections", *Rev. Chir. Ortho.*, 79:299–305 (1993).

Damien, C. J. and Parsons, J. R., Bone Graft and Bone Graft Substitutes: A Review of Current Technology and Application, *J. Appl. Biomat.*, 2:187–208 (1991).

* cited by examiner

*Primary Examiner*—David J. Isabella
(74) *Attorney, Agent, or Firm*—Kohn & Associates, PLLC

(57) ABSTRACT

A monolithic bioresorbable implant includes optimally designed openings to treat tissue disorders or drug delivery. Preferably, the implant is made from calcium salts. A method of filling a recipient treatment site includes the step of disposing the monolithic bioresorbable implant into the site.

17 Claims, 1 Drawing Sheet

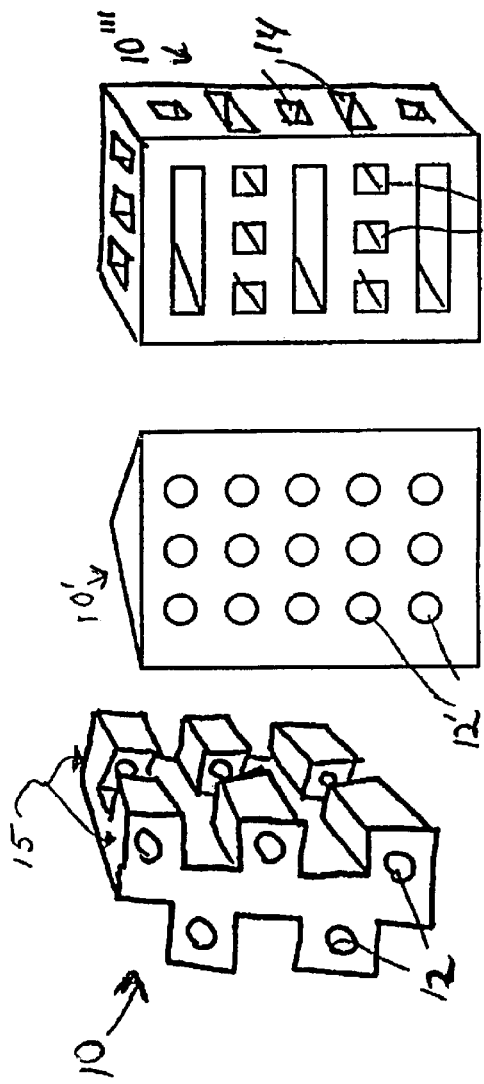
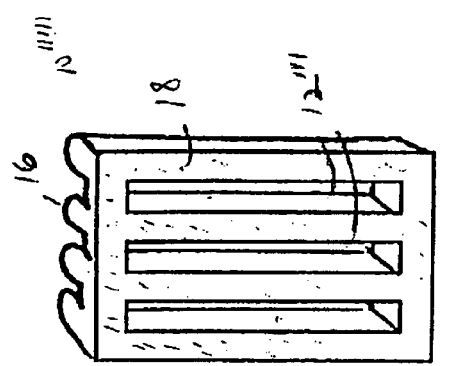

MONOLITHIC IMPLANTS WITH OPENINGS

TECHNICAL FIELD

The present invention generally relates to compositions or devices useful for therapeutic applications. More specifically, the present invention provides a scaffold implant and method of use for tissue regeneration.

BACKGROUND OF THE INVENTION

Much work has been done directed to the goal of finding a suitable material to repair or replace tissue defects. Regarding the skeletal system, Coetze (1980) reported upon the regeneration of bone in the presence of calcium sulfate. Coetze reported that although autogenous bone would be recognized as the ideal grafting material, it is not always available and it cannot be molded in various shapes and sizes. With calcium sulfate, a large mastoid cavity can be eliminated and a new antrium created. Calcium sulfate is available in all countries, is easy to handle, is inexpensive, and above all, is replaced with autogenous bone as nature designed.

The use of bioresorbable bone void filler devices such as calcium sulfate pellets have been reported in the literature for many years. The pellet dimensions vary in size from 4 to 7 mm in diameter and from 3 to 6 mm in thickness. The use of these pellets resulted in satisfactory bone void filling, the pellets resorbing as new bone grew. Pellets were preferred over a solid or compact mass because it was perceived that they would resorb faster, facilitate bone and void filling, and offer more surface area for drug elution. Also, a solid mass would resorb from the outside to the inside, a slow process. However, the main problem remaining with infected or destroyed bone is to replace the bone. The goal is to restore normal bone and replace the normal features. Thus, controlled regeneration of bone is desired.

Several patents have been issued towards achieving the goals mentioned above. For example, U.S. Pat. No. 4,619,655 to Hanker et al., issued Oct. 28, 1986, discloses the use of Plaster of Paris to form implants as well as a bioresorbable scaffold for implants and bone repair in animals. The plaster is mixed with a non-bioresorbable calcium source such as calcium phosphate ceramic to stimulate bone formation. Plaster is also proposed to be used as a medicament implant, encasing the active material for subsequent release in situ.

U.S. Pat. No. 5,147,403 to Gitelis, issued Sep. 15, 1992, discloses a technique for implanting a prosthesis in a host bone by preparing the surface of the host bone to receive the prosthesis, applying calcium sulfate in free-flowing form to the receiving surface of the host bone, and seating the prosthesis in the receiving surface whereby the calcium sulfate fills one or more gaps resulting between the prosthesis and host bone.

U.S. Pat. No. 5,569,308 to Sottosanti, issued Oct. 29, 1996, discloses methods for use in bone tissue regeneration containing a barrier material and a graft material. The barrier material can be calcium sulfate, the graft material being any suitable material, including a composite graft material containing demineralized, freeze dried, allogenic bone, and calcium sulfate.

U.S. Pat. No. 6,614,206 to Randolph et al., issued Mar. 25, 1997, discloses the controlled release of calcium sulfate, as well as the controlled release of an additive to calcium sulfate matrix such as medicaments or pesticides. The controlled release is achieved by a pellet comprising calcium sulfate.

In view of the above, the direction of research and development has gone towards the use of pellets, made from calcium sulfate and possibly containing medicaments or other additives, to provide a bioresorbable scaffolding for implants and to form the implants themselves.

Due to its poor mechanical properties, Plaster of Paris (POP or calcium sulfate) was almost discarded from the biomedical field for the past 30 years. Research was focused on new materials such as HA and collagen (both non-bioresorbable materials), bioresorbable polymers (generally releasing irritant by-products) and the like. These osteoconductive materials were shaped to imitate the porosity of the cancellous bone structure. Porous material structure includes thin partitions of compact material separating empty cells which have an average dimension of more than 100 micrometers. Bone cells were expected to migrate through the porous structure and integrate the implant. Generally, only the periphery of the implant hosts living cells. The core stays untouched if too deep. When these materials are used in a solid or compact form, they are proposed as small pellets or particulate. Solid or compact material is defined as non-porous or micro-porous material; with average pore size less than 20 micrometers. In the case of biodegradable polymers, such as PLA-PGA polymers, a porous structure is also preferred because large quantity of material can become toxic during resorbsion. Sometime, holes were drilled through these porous implants as attachment sites or to facilitate bone cell migration. All large implants observed by applicant were made of porous materials.

Small pellets are hard to handle, implant, locate, and shape into the tissue cavity. Once implanted, they can migrate from the implantation site. Larger pellets are too big to fit small details of the cavity features. They also dissolve slower from outward to inward.

There is a renewed interest in POP. First, it resorbs at a rate comparable to new bone growth and the final result is a cavity filled with actual patient bone instead of a composite new bone-bone void filler material. Second, POP is the only commonly known material which can be implanted in an infected wound (any other material will generate a foreign body reaction). Third, POP is a pure, clean mineral that does not present the imnmunoreaction potential other implants can cause.

It would be advantageous to derive a scaffolding implant having preformed structure but still possessing architectural similarities to the prior art pellet implants discussed above.

SUMMARY OF THE INVENTION AND ADVANTAGES

In accordance with the present invention, there is provided a monolithic compact bioresorbable scaffolding including optimally designed openings to support new tissue regeneration or drug delivery. The present invention further provides methods of making compact monolithic bioresorbable implant, and methods of filling recipient graft sites by disposing monolithic bioresorbable implants in the graft sites.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1 is a perspective view of the first embodiment of the present invention;

FIG. 2 is a second embodiment of the present invention constructed in accordance with the present invention;

FIG. 3 is a third embodiment of the present invention constructed in accordance with the present invention;

FIG. 4 is a fourth embodiment of the present invention constructed in accordance with the present invention; and FIG. 5 is a fifth embodiment of the present invention.

DETAILED DESCRIPTION OF THE INVENTION

A monolithic bioresorbable scaffolding made in accordance with the present invention is generally shown at 10 in FIG. 1. The scaffolding 10 is made of compact material resulting of a molding or compression process described below to form a monolithic structure of desired dimension, size, and shape. The compact or solid material is defined as non-porous or microporous with average pore size less than 20 micrometers.

By scaffolding, it is meant that the present invention provides a supporting matrix in which tissue grows in a predetermined shape, the shape being predetermined by the shape of the scaffolding. The scaffolding is reabsorbed, thereby leaving behind the regenerated tissue. Hence, the implanted scaffolding does, in fact, function as a scaffold to support and shape the regenerated tissue.

The monolithic bioresorbable scaffolding 10 includes openings having specific sizes. This is not an arbitrary selection of opening size, but rather it is a result of a calculation such that the present invention, having a solid self-defined structure, also mimics the physical character of the previously used pellets.

Preformed monolithic scaffoldings with cavities are designed to fit the tissue gaps or cavities to be treated. The openings are designed to imitate the gaps between small pellets which allows tridimensional revascularization and penetration of new tissue cells, favoring tissue regeneration.

More specifically, as discussed above, pellet dimensions vary from 4 to 7 mm in diameter and from 3 to 6 mm in thickness. Applicant has calculated that when spheres of radius R arranged into the most compact situation, the smallest gaps or openings between have a cross sectional area of $0.161\ R^2$. The area covers by the openings corresponds to approximately 9% of the cross sectional area of the sphere assembly.

In this configuration, the volume of the spheres occupies between approximately 68% and 74% of the sphere structure volume. In a similar way, the area covered by openings between by cylindrical pellets of various dimensions is estimated to be between 2% and 60% of the cross sectional area of the pellet assembly according to the configuration of the arrangement (ordered or random). The volume occupies by cylindrical pellets of various dimensions is estimated to be between 40% and 95% of the pellet structure volume.

Applicant has calculated that the surface area of the smallest opening between three spheres of radius R is $0.161\ R^2$. The radius equivalent to such an opening was calculated to be $0.226\ R$. The inscripted circular opening between the three spheres of radius R was calculated to be $0.155\ R$. For spheres with diameters between 4 and 7 mm, the opening radius equivalent was calculated to be between 0.9 and 1.6 mm, respectively: The inscripted opening was calculated to be between 0.6 and 1.1 mm, respectively.

The structure, as illustrated in FIG. 1, also includes openings 12 therein. The opening surface area covers between 2 and 60% of the surface area of structure side where they are located. Circular openings can have a size range between 0.5 and 3 mm in radius or radius equivalent. Preferably, the circular opening size ranges are between 0.9 and 2.5 mm in radius or radius equivalent.

Larger elongated openings can also be useful; they can be included in the compact monolithic devices, the total opening surface area covering between 2% and 60% of at least one device side, as shown in FIG. 5.

The openings 12 can be used for various purposes, such as allowing tissue integration, regenerating tissue cell access, as well as providing for connection point between premolded assemblable blocks.

The openings are critical to the function of the monolithic devices. Prior art monolithic devices and methods allowed only outward to inward bone growth and implant resorbtion. This could result in initial encapsulation of the implant by the growing bone, thereby preventing further resorbtion and bone growth. The openings of the present invention allow for simultaneous inward and outward growth since regenerating tissue cells can enter the monolithic through the openings. The openings 12 can be through holes forming passageways completely through the implant, shown in FIG. 1, or can be blind holes as shown in several of the other figures, such as in the implant 10' in FIG. 2. These openings are indicated as openings 12' and a block having a square face in a triangular cross section.

The openings can take on various configurations relative to the scaffolding. For example, the openings can be in parallel, as shown at 12 in FIG. 1, or they can be perpendicular shown at 12" and 14 in FIG. 3, the implant being indicated as 10'''.

The openings can have various sizes and shapes. Sizes and shapes are a function of the desired results regarding parameters such as specific surgical application, controlled rate of release, or manufacturing process. Various other opening configurations can be used, such as in FIG. 3, where the openings are through openings which interconnect with each other.

A thin tissue gap can be filled with a scaffolding implant having through openings only running in a direction perpendicular to the gap plan. Larger tissue defects can necessitate implants having interconnected openings to allow tridimensional growth of new tissues.

The spacing of the openings can be varied according to need and result. For example, openings can be separated by a distance of between 0.10 to 20.0 mm. Preferably, the openings are separated by a distance of 1.0 to 5.0 mm, thus mimicking the thickness dimensions of prior art pellets.

The overall shape of the scaffolding can take on various forms. For example, implant 10 in FIG. 1 has a complex design with various protrusions which are symmetric. However, the protrusions need not be symmetric, the shape merely depending upon the mold shape used. Therefore, a triangular block configuration of the present invention is shown in FIG. 2 while a rectangular version is shown in FIG. 3. The device can include a curved surface as shown in the oval shaped device 10.4' shown in FIG. 4 or can have a complex shape as shown in FIG. 5 at 10.5', wherein the device includes a wavy surface 16 on one size and a flat surface 18 on an opposite side, including through holes 12'''. The surface itself can be smooth as shown in FIG. 1-4 or could have a rough configuration on at least part of the surface as shown in FIG. 5 on the flat surface 18 thereof.

As stated above, the present invention is made of a compact material, preferably consisting essentially of calcium salt. The salt can be calcium sulfate, tricalcium phosphate or a mixture of both. The devices can be manufactured prior to surgery or, in some cases, in situ during surgery. The devices can be made by the following processes.

In a first example of the manufacturing process, a mixture made of calcium sulfate hemihydrate powder and possible additive materials is mixed with an aqueous solution to form a paste. The aqueous solution can contain set time modifiers such as potassium sulfate or borates. The paste is then poured into a mold cavity having the desired overall shape. The paste is then poured into a mold cavity having the desired overall shape. After a certain amount of time, generally between 2 and 30 minutes, the paste solidifies into a compact material. The openings can either be directly formed during the molding process, drilled later, or resulting of the assemblage of molded parts.

In a second example of the manufacturing process, a mixture made of calcium salt powder and possible additive materials is compressed using a press in a die having the desired overall shape The applied pressure has for effect to compact the powder into a solid device. The openings can either be directly formed during the compression process, drilled later, or resulting of the assemblage of molded parts.

In a third example of the manufacturing process, a mixture made of calcium sulfate hemihydrate powder and possible additive materials is mixed with an aqueous solution to form a paste. The aqueous solution can contain set time modifiers such as potassium sulfate or borates. The paste is then loaded into extrusion equipment. Flexible rods of solidifying paste are then extruded into a cavity having the desired overall shape. The monolithic device is built layers by layers by controlling the motion of the extrusion head. After a certain amount of time, generally between 2 and 30 minutes, the paste solidify into a compact material including openings between the extruded rods.

The scaffolding consists of between 40 to 95 percent of compact material by size. That is, the device consists of compact areas and opening areas. Preferably, the implant consists of between 65 to 80 percent of compact material, the remaining area being openings.

Although the scaffolding consists essentially of calcium salt in a compact for, it can include additives selected from the group including additives such as collagen fibers, demineralized bone matrix, medicaments, and growth factors, as well as other additives known in the art to be previously added to various calcium sulfate pellet implants. The medicaments can be drugs such as antibiotics, analgesics, antiinflammatory agents, antiviral agents, and/or antineoplastic agents, as well as other agents well known in the art. The design of the openings, exposing further surface area of the implant, can result in changes in the pharmaceutical kinetics of the release of the medicaments as well as other additives.

Thus, the scaffolding can be designed with increased opening surfaces and areas of needed increased release, such as in specific infected areas, as well as increasing or decreasing the amount or positioning of openings for other reasons known to those in the art such as for regenerating tissue cell access, etc.

In view of the above, the present invention provides a method of filling a recipient treatment site by disposing monolithic bioresorbable implant made in accordance with the present invention in the site.

As an example, in the treatment of tissue disorders, the diseased tissues are usually removed. The resulting cavity usually needs to be filled. One or several monolithic devices with openings can be placed into the tissue cavity to restore the normal tissue features while allowing tissue regeneration. The cavity is then closed following standard procedures. The device will resorb as the new tissues fill the cavity.

As stated above, the present invention can be custom molded to the desired shape to specifically fill the site. The implant is either being formed in situ or formed prior to surgery and disposed into the site in accordance with the present invention as stated above.

As an example, a formed in situ custom scaffolding can be produced by the following technique; a mixture made of calcium sulfate hemihydrate powder and possible additive material is mixed with an aqueous solution to form a paste. The paste is then poured into a tissue cavity to be treated. Then rods of appropriate dimensions are inserted into the paste and maintained still until the paste solidifies into a compact material. The rods are then removed and the cavity is closed following standard procedures. The device will resorb as the new tissues fill the cavity.

The inventive method can also include the step of extruding a part into rods or spaghetti-like strips which solidifies into the compact mass, as discussed above.

Also as stated above, the present inventive method can be achieved by attaching preformed parts of the implant. These preformed parts can be attached together by various methods known in the art, such as by utilizing adhesive or mechanical means. Such an adhesive can be selected from the group including calcium based slurries or bioresorbable organic adhesives (such as cyanoacrylates). Such a mechanical mean can be a bioresorbable screw, tack, or suture.

A further alternative method is to compress particles into a form to form a preformed part. The part alone, or multiple parts, can be disposed into the site. Multiple parts may be connected, as discussed above. Compression of pellets or the like is well known in the forming art.

In view of the above, the present invention can find utility in all uses in which previously used regenerative tissue scaffolds have been reported. For example, the device can be used as a bone graft extender, a bone graft substitute, a bone void filler, a soft tissue barrier, a cell scaffold, a drug delivery device, for bone defect treatment, bone fusion, reconstructive surgery, plastic surgery, or treatments of any other tissue disorder.

The following is an example demonstrating the utility of the present invention. The example demonstrates the influence of percent opening area, relative to one side of the implant, and hole diameter on the rate of dynamic dissolution of POP implants. POP parallelepiped devices (2.5 cm×1.8 cm×0.6 cm) were prepared with different numbers of holes of different diameters on their largest sides (4.5 cm$^2$). The devices were placed on a grid immersed in a circulated water bath maintained at 37° C. Every day the devices were removed from the water and dried to constant weight. Their weights were recorded and the devices were replaced in the water bath until the next measurement. The results are summarized in Tables 1 and 2. The data demonstrate that the larger the percent opening area, the faster the dissolution. Also, for the same percent opening area, the larger the hole diameter, the slower the dissolution.

TABLE 1

Sample mass vs. dissolution time

| SAMPLE ID | HOLE DIA-METER | No. OF HOLES | % OPENING AREA | DISSOLUTION DAYS 0 | 1 | 2 |
|---|---|---|---|---|---|---|
| A | 0.0 | 0 | 0% | 3.6773 | 2.3129 | 1.5657 |
| B | 2.0 | 13 | 9% | 3.2568 | 1.9304 | 0.6056 |
| C | 2.0 | 20 | 14% | 3.4063 | 1.8296 | 0.5011 |
| D | 2.0 | 40 | 27% | 3.7334 | 0.9525 | 0.0882 |
| E | 3.6 | 4 | 9% | 3.4223 | 2.0871 | 1.2314 |
| F | 3.6 | 8 | 18% | 2.9067 | 1.8058 | 0.7533 |
| G | 3.6 | 12 | 27% | 2.4999 | 1.2776 | 0.4080 |
| H | 5.1 | 2 | 9% | 4.2176 | 2.5869 | 1.5892 |
| I | 5.1 | 5 | 23% | 3.3922 | 1.8903 | 0.9614 |
| J | 5.1 | 7 | 33% | 2.6541 | 1.3520 | 0.6738 |
| K | 7.2 | 1 | 9% | 3.7879 | 2.3654 | 1.5022 |
| L | 7.2 | 2 | 18% | 3.5740 | 2.1744 | 1.4041 |
| M | 7.2 | 3 | 27% | 3.4953 | 1.8957 | 1.0363 |

TABLE 2

% residual mass vs. dissolution time

| SAMPLE ID | HOLE DIAMETER | % OPENING AREA | DISSOLUTION DAYS 0 | 1 | 2 |
|---|---|---|---|---|---|
| A | 0.0 | 0% | 100% | 63% | 43% |
| B | 2.0 | 9% | 100% | 59% | 19% |
| C | 2.0 | 14% | 100% | 54% | 15% |
| D | 2.0 | 27% | 100% | 26% | 2% |
| E | 3.6 | 9% | 100% | 61% | 36% |
| F | 3.6 | 18% | 100% | 55% | 26% |
| G | 3.6 | 27% | 100% | 51% | 16% |
| H | 5.1 | 9% | 100% | 61% | 37% |
| I | 5.1 | 23% | 100% | 56% | 28% |
| J | 5.1 | 33% | 100% | 51% | 25% |
| K | 7.2 | 9% | 100% | 62% | 40% |
| L | 7.2 | 18% | 100% | 61% | 39% |
| M | 7.2 | 27% | 100% | 54% | 30% |

Throughout this application, various publications are referenced by authors and years. Full citations for the publication are listed below. The disclosure of these publications in their entireties are hereby incorporated by reference into this application in order to more fully describe the state of the art to which this invention pertains.

The invention has been described in an illustrative manner, and it is to be understood the terminology used is intended to be in the nature of the description rather than of limitation.

Obviously, many modifications and variations of the present invention are possible in light of the above teachings. Therefore, it is to be understood that within the scope of the appended claims, reference numerals are numerals are merely for convenience and are not to be in any way limiting, the invention may be practiced otherwise than as specifically described.

References Cited

Coetze, A. S. et al., "Regeneration of Bone in the Presence of Calcium Sulfate", *Arch Otolaryngol*, 106:405–409 (1980)

Bouillet, R. et al., "Traitement de L'Osteomyelete Chronique en Milieu Africain Par Implant De Platre Impregne D'; antibiotiques", *Acta Orthopaedica Belgica*, 55:1–11 (1989)

Macket, D. et al., "Antibiotic Loaded Plaster of Paris Pellets", *Clin. Ortho. and Rel. Res.*, 167:263–268 (1982)

Peltier, L. et al., "Calcium Sulfate" in *Bone Graft and Bone Substitute*, Chapter 22:243–246 (1993)

Sulo, I, "The Use of Gentamycin Impregnated Plaster Beads in the Treatment of Bone Infections", *Rev. Chir. Ortho.*, 79:299–305 (1993)

Damien, C. J. and Parsons, J. R., "Bone Graft and Bone Graft Substitutes: A Review of Current Technology and Application, *J. Appl. Biomat*, 2:187–208 (1991)

What is claimed is:

1. A monolithic bioresorbable scaffolding comprising calcium sulfate hemihydrate material including openings therein for supporting tissue regeneration wherein at least some of said openings are through holes forming passageways completely through said scaffolding and wherein said openings are separated by a distance for controlling the resorption rate of said scaffolding based upon the size and distribution of said openings, said scaffolding promoting three dimensional tissue regeneration and device resorption which results in the replacement of the device by new regenerated tissue throughout the three dimensional structure of the device.

2. A monolithic bioresorbable scaffolding of claim 1 wherein said scaffolding has at least one side including openings covering between 2 to 60 percent of said side.

3. A monolithic bioresorbable scaffolding of claim 1 wherein said opening preferably cover 9 to 30 percent of said side.

4. A monolithic bioresorbable scaffolding of claim 1 wherein said scaffolding consists of between 40 to 95 percent compact material by size.

5. A monolithic bioresorbable scaffolding of claim 4 wherein said scaffolding consists of between 65 to 80% compact material by size.

6. A monolithic bioresorbable scaffolding of claim 1 wherein at least some of said openings are through holes forming passageways completely through said scaffolding.

7. A monolithic bioresorbable scaffolding of claim 1 wherein at least some of said openings are blind holes.

8. A monolithic bioresorbable scaffolding of claim 1 wherein each of said openings define an axis through said scaffolding, said opening axes being nonparallel.

9. A monolithic bioresorbable scaffolding of claim 8, wherein at least two of said openings interconnect with each other.

10. A monolithic bioresorbable scaffolding of claim 1 wherein said openings are separated by a distance of between 0.10 to 20.0 mm.

11. A monolithic bioresorbable scaffolding of claim 10 wherein said openings are separated by a distance of between 1.0 to 5.0 mm.

12. A monolithic bioresorbable scaffolding of claim 1 wherein said scaffolding consists essentially of calcium salt.

13. A monolithic bioresorbable scaffolding of claim 12 wherein said salt is calcium sulfate, tricalcium phosphate or a mixture of both.

14. A monolithic bioresorbable scaffolding of claim 1 wherein said scaffolding further includes additives selected from the group consisting of hydroxy apatite, collagen fibers, demineralized bone matrix, medicaments, and growth factors.

15. A monolithic bioresorbable scaffolding of claim 14 wherein said medicaments can be selected from the group consisting of antibiotics, analgesics, anti-inflammatory agents, antiviral agents, and/or antineoplastic agents.

16. A method of filling recipient treated sites comprising the step of disposing a compact monolithic bioresorbable scaffolding of claim 1 in the treated site.

17. A method of filling recipient treated sites of claim 16 wherein a plurality of the scaffolding are disposed in the treated site.

* * * * *